(12) United States Patent
Phinney et al.

(10) Patent No.: US 7,025,348 B2
(45) Date of Patent: Apr. 11, 2006

(54) METHOD AND APPARATUS FOR DETECTION OF MULTIPLE DOCUMENTS IN A DOCUMENT SCANNER USING MULTIPLE ULTRASONIC SENSORS

(75) Inventors: Jennifer J. Phinney, Rochester, NY (US); Daniel P. Phinney, Rochester, NY (US); David M. Pultorak, Rochester, NY (US); Nelson A. Blish, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 344 days.

(21) Appl. No.: 10/303,263

(22) Filed: Nov. 25, 2002

(65) Prior Publication Data
US 2004/0100018 A1 May 27, 2004

(51) Int. Cl.
*B65H 7/12* (2006.01)
(52) U.S. Cl. ............... 271/262; 271/263; 271/265.04; 367/93; 367/125
(58) Field of Classification Search ............... 271/262, 271/263, 265.04; 340/673, 674; 367/93, 367/125; 73/159, 1.82, 587, 589, 602, 603, 73/632, 645
See application file for complete search history.

(56) References Cited

U.S. PATENT DOCUMENTS

| | | | |
|---|---|---|---|
| 4,066,969 A * | 1/1978 | Pearce et al. ............... 367/125 |
| 4,368,438 A | 1/1983 | Stienstra |
| 4,693,010 A | 9/1987 | Sills |
| 5,067,704 A * | 11/1991 | Tsuihiji et al. ............... 271/262 |
| 5,560,598 A * | 10/1996 | Goldkuhle ................... 271/263 |
| 5,823,529 A * | 10/1998 | Mandel et al. ............... 271/296 |
| 6,069,681 A * | 5/2000 | Nakagawa et al. ........... 355/23 |
| 6,212,130 B1 * | 4/2001 | Brazeal et al. ................ 367/93 |
| 6,397,671 B1 * | 6/2002 | Nishio et al. .................. 73/159 |
| 6,511,064 B1 * | 1/2003 | Phinney et al. ............. 271/262 |
| 6,761,352 B1 * | 7/2004 | Scicluna et al. ............ 271/153 |
| 2003/0094748 A1 * | 5/2003 | Chujo et al. ................ 271/262 |

FOREIGN PATENT DOCUMENTS

| | | |
|---|---|---|
| DE | 36 20 042 A1 | 1/1987 |
| DE | 197 01 644 A1 | 7/1998 |
| DE | 198 52 719 A1 | 6/1999 |
| EP | 1 148 012 A2 | 10/2001 |

* cited by examiner

Primary Examiner—David H. Bollinger
(74) Attorney, Agent, or Firm—Nelson Adrian Blish

(57) ABSTRACT

An apparatus (10) for detection of multiple documents (42) in a document transport system comprises a first transmitter (13) emitting a first signal at a first interval through a document feed path (40). A first sensor (14) detects the first signal from the first transmitter (13). A second transmitter (15) emits a second signal at a second interval through the document feed path (40). A second sensor (16) detects the second signal from the second transmitter (15).

24 Claims, 2 Drawing Sheets

METHOD AND APPARATUS FOR DETECTION OF MULTIPLE DOCUMENTS IN A DOCUMENT SCANNER USING MULTIPLE ULTRASONIC SENSORS

FIELD OF THE INVENTION

This invention relates in general to using multiple detectors for sensing multiple document feeds or small documents overlapped with larger documents.

BACKGROUND OF THE INVENTION

Scanners and copiers use document feeders to transport documents into the machine. Mechanisms used for the transportation of documents, including paper or sheets of other material, have the capacity to accidentally pick up more than one document fed from a stack of documents. It is necessary to determine when more than one document is pulled into a document transport since multiple documents may jam the transport or prevent processing some documents. In many cases, the documents fed into the scanner are different sizes. Some smaller documents may be located on one side of a document feed path and not pass under a single position sensor.

There are two general methods for multiple document detection, contact and non-contact. The contact methods include measurement of small thickness changes with a contact foot or sensing arm that is in contact with the documents as they pass through the document transport. The contact foot is connected to a linear voltage differential transducer (LVDT), or a magnet, which is sensed by a Hall Effect Sensor. These sensors can detect changes in thickness of less than 1 μm ($10^{-6}$ m).

The major disadvantage to the contact method is that anything in contact with moving paper, especially thin paper or ripped paper, can cause a malfunction such as a paper jam. The contact method also requires calibration using the maximum thickness document that will be fed through the document transport. When a thickness is measured which is above the calibration value plus a threshold, typically 30%, it is determined to be a multiple document feed. This method, however, will only work when documents having a uniform thickness are processed. Using a wheel on the end of the contact foot can reduce the chances of paper jam, however, the variations in the diameter of this wheel, due to the nonconformity in manufacturing, must be taken into account during the measurements.

The primary non-contact method for multiple document detection sends ultrasound signals through the document stream to determine if more than one document is present. Sending ultrasound through paper results in attenuation of the ultrasound signal. It is possible to determine the presence of multiple documents by change in attenuation of the signal received. This method is independent of the thickness of the individual documents and is made without making contact with these documents.

There are currently ultrasonic detection system available, which use high frequency sensors to sense multiple zones within a local area. This approach works because the sensors are directional, and the signal from one sensor does not interfere with the signal from other sensors. However, these sensors are also more expensive. Low cost sensors have a wide angle of energy emitted, and if used, the sensors can interfere with each other (cross-talk). The interference often causes the design to fail. The problem cannot be solved by multiplexing individual pulses to the emitters, because not enough energy will be sent by the detector and the time phasing of the signal is not stable.

U.S. Pat. No. 6,212,130 uses a tilted ultrasonic sensor. This could be used in multiple locations but the cost would be significant, using the more expensive directional high frequency sensors.

SUMMARY OF THE INVENTION

The present invention provides an improved method and apparatus for multiple document detection, which is both accurate and relatively inexpensive, over a wide area. The interference between the sensors is limited by allowing only one transmitter and receiver pair to be on at once.

Briefly, according to one aspect of the present invention an apparatus for detection of multiple documents in a document transport system comprises a first transmitter emitting a first signal at a first interval through a document feed path. A first sensor detects the first signal from the first transmitter. A second transmitter emits a second signal at a second interval through the document feed path. A second sensor detects the second signal from the second transmitter.

An aspect of the present invention is maintaining the phase signal from the sensors stable when being turned on and off by applying multiple cycles to the transmitter. In one embodiment of the invention, 100 cycles of the emitting frequency creates almost the same amount of energy as a continuously operational sensor. By transmitting multiple cycles of the transmitter and then multiplexing those times between sensors, multiple sensors may be used to reliably sense documents. Signal from the active sensor can then be sampled at specific times, when the other sensors are turned off. Therefore, these sensors may be multiplexed reliably and used to sense multiple zones for multiple document detection.

The invention and its objects and advantages will become more apparent in the detailed description of the preferred embodiment presented below.

DETAILED DESCRIPTION OF THE INVENTION

The present invention will be directed in particular to elements forming part of, or in cooperation more directly with the apparatus in accordance with the present invention. It is to be understood that elements not specifically shown or described may take various forms well known to those skilled in the art.

Figure 1:
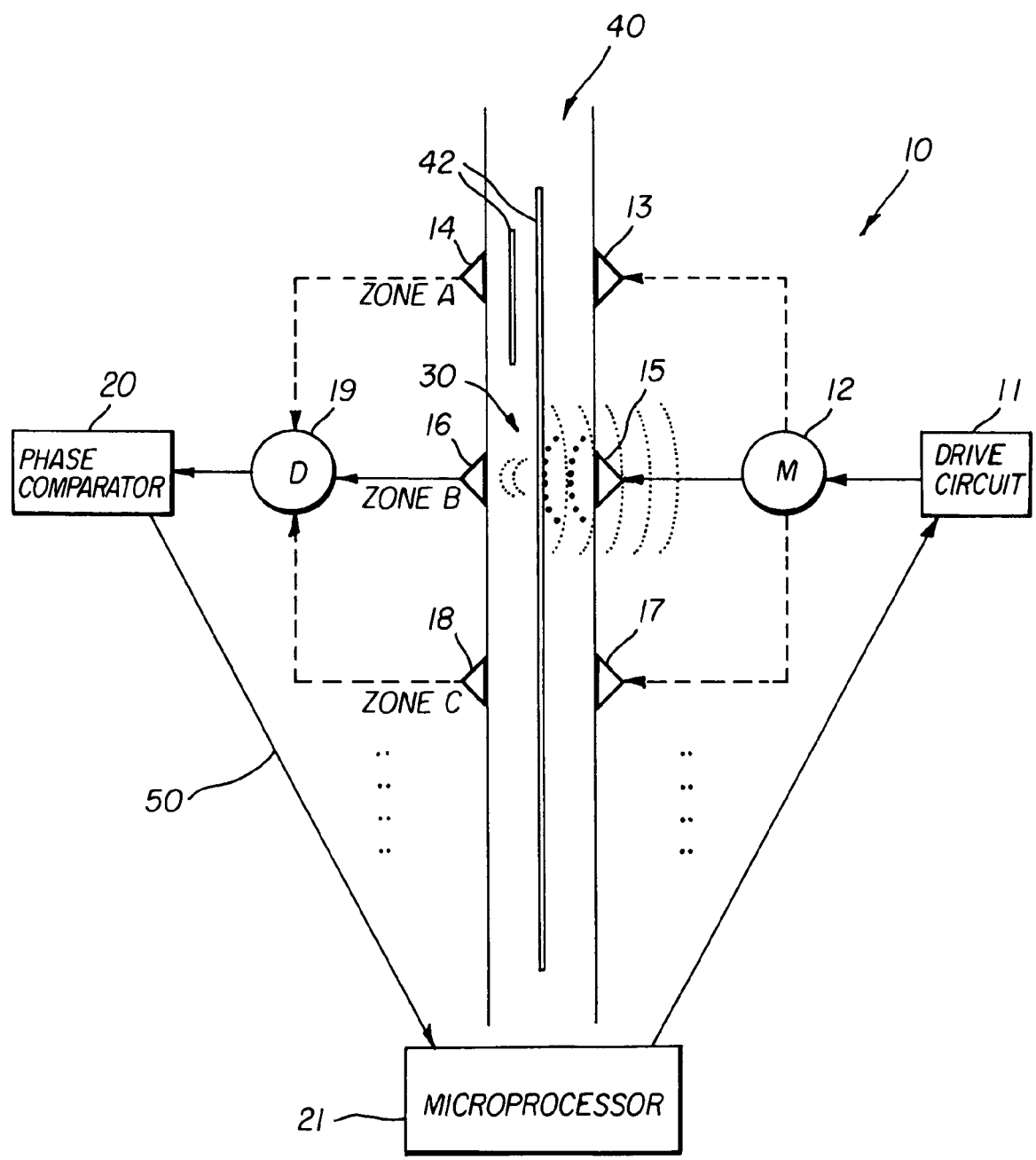
FIG. 1 is a schematic diagram showing paper passing through the system with a double passing through zone A.

Referring now to FIG. 1, an apparatus for multiple document detection 10 in accordance with one embodiment of the present invention is shown. In this particular embodiment, the apparatus includes an ultrasonic drive circuit 11, which provides a drive signal to a multiplexer 12, which sends the signal to the appropriate transmitter, for example transmitter 15, as determined by the microprocessor 21. The ultrasonic transmitter produces an ultrasonic signal 30 that passes through a document feed area 40, which comprises one or more documents 42 and is received by the appropriate ultrasonic receiver, for example receiver 16, as determined by the microprocessor 21. A phase shift of the ultrasonic signal is relatively independent of the thickness of the document or documents in the document feed. This results in a received ultrasonic signal with a phase shift approximately dependent on only the number of documents in the document feed, because of the interfaces between different materials through which the ultrasound passes causes the phase shift, not the total thickness of the documents.

The ultrasonic receiver 16 converts the received ultrasonic signal into an electrical signal. The electronic signal is sent to a demultiplexer 19 and then supplied to an input to a phase comparator 20 wherein the phase difference between the drive signal and the electronic signal is determined. An information signal 50 which represents the determined phase difference is fed from phase comparator 20 to a microprocessor 21.

The microprocessor 21 checks the appropriate information signal, after about 100 cycles, to determine if multiple documents are present based on the resulting phase shift or difference between the drive signal and the electronic signal. The microprocessor 21 switches to a different set of transmitters and receivers, for example transmitter 17 and receiver 18, and repeats the process continuously between the sets. In a similar fashion, the microprocessor 21 checks for double document feed between transmitter 13 and receiver 14. In this embodiment only one set of transmitters and receivers are energized at any particular time, although other sequencing schemes are possible.

Although a microprocessor 21 is shown, other types of processors or programmable devices can also be used. Additionally, although in this particular example, an ultrasonic signal is used in this apparatus, other types of signals can also be used.

Figure 2:
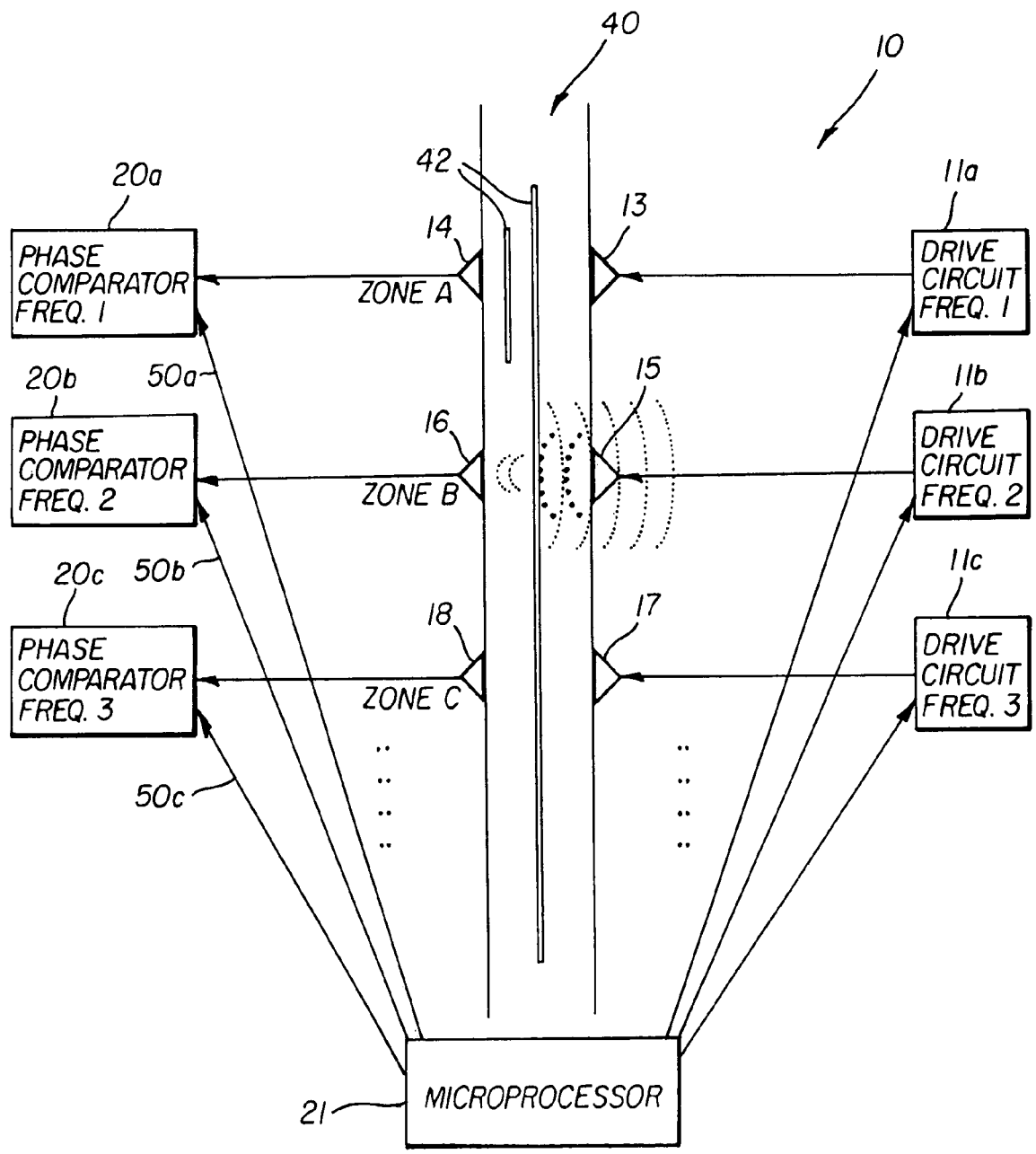
FIG. 2 s a schematic view showing transmitters operating at different frequencies.

Referring now to FIG. 2, an alternate embodiment of the invention is shown wherein transmitters 13, 15, and 17 operate at different frequencies. Operating the transmitters at different frequencies eliminates the problem mutual interference in the signals received at receivers 14, 16, and 18 when all transmitters are operated concurrently. Multiple drive circuits 11*a*, 11*b*, and 11*c* may be used to drive the individual transmitters. Multiple phase comparator circuits 20*a*, 20*b*, and 20*c* may be used to determine the phase. The frequency for the various transmitters should be separated by at least a gap of 5 MHz, although different modulation schemes are possible.

The invention has been described in detail with particular reference to certain preferred embodiments thereof, but it will be understood that variations and modifications can be effected within the scope of the invention.

PARTS LIST

10. Multiple document detection
11. Ultrasonic drive circuit
11*a*. Drive circuit
11*b*. Drive circuit
11*c*. Drive circuit
12. Multiplexer
13. Transmitter
14. Receiver
15. Transmitter
16. Receiver
17. Transmitter
18. Receiver
19. Demultiplexer
20. Phase comparator
20*a*. Phase comparator
20*b*. Phase comparator
20*c*. Phase comparator
21. Microprocessor
30. Ultrasonic signal
40. Document feed area
42. Documents
50. Information signal

What is claimed is:

1. An apparatus for detection of multiple documents in a document transport system comprising:
    a first transmitter emitting a first signal for a first interval through a document feed path;
    a first sensor for detecting said first signal from said first transmitter;
    a second transmitter for emitting a second signal for a second interval through said document feed path;
    a second sensor for detecting said second signal from said second transmitter; and
    wherein said first signal is an ultrasonic signal.

2. An apparatus as in claim 1 wherein said first interval does not overlap said second interval.

3. An apparatus as in claim 1 wherein said first transmitter and said second transmitter are separated by at least one-half a width of said feed path.

4. An apparatus as in claim 1 wherein said first and second signal are at a common frequency.

5. An apparatus for detection of multiple documents in a document transport system comprising:
    a first transmitter emitting a first signal for a first interval through a document feed path;
    a first sensor for detecting said first signal from said first transmitter;
    a second transmitter for emitting a second signal for a second interval through said document feed path;
    a second sensor for detecting said second signal from said second transmitter;
    a third transmitter for a emitting a third signal for a third interval through said document feed path; and
    a third sensor for detecting said third signal from said third transmitter.

6. An apparatus as in claim 5 wherein said first, second, and third signals are ultrasonic signals.

7. An apparatus as in claim 5 wherein said first, second, and third intervals do not overlap.

8. An apparatus for detection of multiple documents in a document transport system comprising:
    a first transmitter emitting a first signal for a first interval through a document feed path;
    a first sensor for detecting said first signal from said first transmitter;
    a second transmitter for emitting a second signal for a second interval through said document feed path;
    a second sensor for detecting said second signal from said second transmitter;
    a third transmitter for a emitting a third signal for a third interval through said document feed path;
    a third sensor for detecting said third signal from said third transmitter; and
    wherein said first, second, and third transmitters are equally spaced across said feed path.

9. An apparatus for detection of multiple documents in a document transport system comprising:
    a first transmitter emitting a first signal at a first frequency through a document feed path;
    a first sensor for detecting said first signal from said first transmitter;
    a second transmitter for emitting a second signal at a second frequency through said document feed path; and a second sensor for detecting said second signal from said second transmitter.

10. An apparatus as in claim 9 wherein said first signal is an ultrasonic signal.

11. An apparatus as in claim 9 wherein said first frequency is at least five kHz greater than said second frequency.

12. An apparatus as in claim 9 wherein said first frequency is approximately 40 kHz.

13. An apparatus as in claim 9 wherein said first transmitter and said second transmitter are separated by at least one-half a width of said feed path.

14. An apparatus as in claim 9 comprising:
a third transmitter for a emitting a third signal at a third frequency through said document feed path; and
a third sensor for detecting said third signal from said third transmitter.

15. An apparatus as in claim 14 wherein said first, second, and third signals are ultrasonic signals.

16. An apparatus as in claim 14 wherein said first, second, and third frequencies do not overlap.

17. An apparatus as in claim 14 wherein each of said frequencies is less than two MHz.

18. An apparatus as in claim 14 wherein said first, second, and third transmitters are equally spaced across said feed path.

19. A method for detection of multiple documents in a document transport system comprising the steps of:
emitting a first signal for a first interval through a document feed path;
detecting said first signal;
emitting a second signal for a second interval through said document feed path;
detecting said second signal; and
wherein said first signal is an ultrasonic signal.

20. The method of claim 19 wherein said first interval does not overlap said second interval.

21. The method of claim 19 wherein a first transmitter and a second transmitter for emitting said first signal and said second signal are separated by at least one-half a width of said feed path.

22. A method for detection of multiple documents in a document transport system comprising the steps of:
emitting a first signal for a first interval through a document feed path;
detecting said first signal;
emitting a second signal for a second interval through said document feed path;
detecting said second signal;
comprising the further step of:
emitting a third signal for a third interval through said document feed path; and
detecting said third signal from said third transmitter.

23. The method of claim 22 wherein said first, second, and third signals are ultrasonic signals.

24. The method of claim 22 wherein said first, second, and third intervals do not overlap.

* * * * *